United States Patent
Calimente et al.

(10) Patent No.: US 9,926,338 B2
(45) Date of Patent: Mar. 27, 2018

(54) CARBOXYLIC ACID FUNCTIONAL SILOXANES OF DEFINED STRUCTURE

(71) Applicant: WACKER CHEMICAL CORPORATION, Adrian, MI (US)

(72) Inventors: Daniel Calimente, Saline, MI (US); Timothy McCormack, Ypsilanti (MA)

(73) Assignee: WACKER CHEMICAL CORPORATION, Adrian, MI (US)

(*) Notice: Subject to any disclaimer, the term of this patent is extended or adjusted under 35 U.S.C. 154(b) by 0 days.

(21) Appl. No.: 14/722,485

(22) Filed: May 27, 2015

(65) Prior Publication Data

US 2016/0347775 A1    Dec. 1, 2016

(51) Int. Cl.
| | | |
|---|---|---|
| C07F 7/08 | (2006.01) |
| C08G 77/38 | (2006.01) |
| C08L 83/06 | (2006.01) |
| C08G 77/50 | (2006.01) |
| C08L 83/14 | (2006.01) |

(52) U.S. Cl.
CPC ............ C07F 7/087 (2013.01); C07F 7/0889 (2013.01); C08G 77/38 (2013.01); C08G 77/50 (2013.01); C08L 83/06 (2013.01); C08L 83/14 (2013.01)

(58) Field of Classification Search
CPC ........ C07F 7/087; C07F 7/0889; C08G 77/38; C08L 83/06
See application file for complete search history.

(56) References Cited

U.S. PATENT DOCUMENTS

| 4,496,687 A | 1/1985 | Okada et al. |
| 4,795,680 A | 1/1989 | Rich et al. |
| 5,399,652 A | 3/1995 | Bindl et al. |
| 6,784,244 B1 | 8/2004 | Linzell |
| 2004/0155220 A1 | 8/2004 | Buskies et al. |
| 2010/0016501 A1 | 1/2010 | O'Lenick et al. |

FOREIGN PATENT DOCUMENTS

| CN | 103074029 A | 5/2013 |
| GB | 2168065 A | 6/1986 |
| WO | 2015/066165 A1 | 5/2015 |
| WO | 2015/066199 A1 | 5/2015 |

OTHER PUBLICATIONS

Pinteala, M., et al, "Functional Polysiloxanes" 2. "On the reaction of hydroxypropyl- amdn aminoalkyl0terminated polydimethylsiloxanes with cyclic anhydrides," Polymer Bulletin, Springer, Heidelberg, DE, vol. 32, No. 2, Feb. 1, 1994, pp. 173-178, vol. 2.

*Primary Examiner* — Jessee Roe
*Assistant Examiner* — Alexander Polyansky
(74) *Attorney, Agent, or Firm* — Brooks Kushman P.C.

(57) ABSTRACT

Organopolysiloxanes bearing regularly spaced pendent carboxylic acid groups or salts thereof have a block polymer structure and are derived by the double half-esterification of a dianhydride and a silanol- or carbinol-functional organopolysiloxane or sulfur analog thereof. The products can form stable aqueous dispersions without the need for a surfactant.

20 Claims, No Drawings the invention pertains to carboxylic acid functional organopolysiloxanes of defined structure, which are preferably self-emulsifiable, either as such, or in the form of salts thereof. The organopolysiloxanes contain pendent, regularly spaced carboxylic acid groups or salts thereof, and in-chain ester linkages.

CARBOXYLIC ACID FUNCTIONAL SILOXANES OF DEFINED STRUCTURE

BACKGROUND OF THE INVENTION

1. Field of the Invention

The invention pertains to carboxylic acid functional organopolysiloxanes of defined structure, which are preferably self-emulsifiable, either as such, or in the form of salts thereof. The organopolysiloxanes contain pendent, regularly spaced carboxylic acid groups or salts thereof, and in-chain ester linkages.

2. Description of the Related Art

Emulsions and dispersions of polyorganosiloxanes ("silicones") have a myriad of uses. For silicones bearing only non-polar and/or non-functional groups, e.g. polydimethylsiloxanes, these exceptionally hydrophobic silicones are not emulsifiable nor dispersible (when solid) by themselves in aqueous compositions. In order to form emulsions or dispersions, surfactants are added, and the silicones are then emulsified, generally under high shear. A wide variety of silicone particle sizes can be created, depending upon the shear exerted upon mixing, the amount and type of surfactant, etc. Such emulsions (hereinafter including dispersions except as noted) are well known in the art and are available commercially from numerous sources. The surfactants used may be non-ionic, Gemini-type, anionic, cationic, zwitterionic, etc. Mixtures of surfactants, e.g. mixtures of non-ionic surfactants having different HLBs, or mixtures of non-ionic surfactants with either anionic, cationic, or other surfactants, are all known.

A problem with surfactant-stabilized silicone emulsions is that they are sometimes prone to separation, which may be observed as an opaque phase ("creaming") or an oily phase. Special mixtures and/or amounts of surfactants can sometimes alleviate this problem. A more difficult problem is separation due to temperature fluctuations, particularly freeze/thaw cycles. A third problem is the presence of the surfactant itself. Since surfactants necessarily have a hydrophilic component, this hydrophilic component, especially in emulsions having a large surfactant content, can cause unwanted water absorption after use, for example when used as a lubricating or surface-modifying component in compositions such as hard surface polishes. In addition, in some applications, surfactants simply cannot be tolerated at all.

To address these problems, so-called "self-emulsifying" silicones have been developed. Such self-emulsifying silicones can form stable emulsions with less surfactant, or even with no surfactant. Hence, the freeze/thaw stability is increased and water absorption/susceptibility is decreased.

Examples of self-emulsifying silicones are the aminoalkyl-terminated silicones, such as aminopropyl- or N-(2-aminoethyl)-3-aminopropyl-terminated polydimethyl siloxanes. Such amino-functional silicones can be prepared by hydrosilylation of, for example, an aminoalkene such as allylamine, with a silicone bearing hydrogendimethylsilyl terminal groups. When protonated, for example by an inorganic acid or organic carboxylic or sulfonic acid, etc., some degree of self-emulsification is achieved. The degree of self-emulsification decreases with increasing organopolysiloxane chain length. To achieve greater self-emulsifying properties, pendent aminoalkyl groups can be introduced along the polymer chain. There are several methods for incorporating pendent aminoalkyl groups, but these all require equilibration at some stage, and thus, the pendent aminoalkyl groups are randomly distributed.

In like fashion, functional silicones with full or partial self-emulsifying properties have been prepared by hydrosilylation to incorporate terminal and/or pendent glycosidyl groups, acryloyl or methacryloyl groups, or polyoxyalkylene groups. Silicones bearing internal, in-chain polyoxyalkylene groups have also been proposed. Silicones containing internal and pendent polyoxyalkylene groups have long been used neat as pore-stabilizing surfactants in polyurethane foam systems.

Such "self-emulsifiable" silicones thus either contained in-chain non-ionic surfactant groups, or pendent emulsifying groups which, again, were randomly distributed.

The random distribution of emulsifying groups in silicones is problematic. Not only are the emulsifying properties less predictable, due to the randomness of the placement of emulsifying groups, but in any mixture of such silicones, there will be a wide range of emulsification properties, even theoretically including some polymer molecules with few if any emulsifying groups. This characteristic may make aqueous emulsions more prone to separation, in particular, to creaming.

It would be desirable to provide self-emulsifying silicones with pendent emulsifying groups with regular, rather than random, positioning. At the same time, such self-emulsifying silicones should be capable of economic preparation, using commercially available or easily synthesized precursors.

SUMMARY

It has now been surprisingly and unexpectedly discovered that silicones having regularly spaced pendent carboxyl groups and also, optionally, terminal carboxyl groups (and salts thereof) may be prepared by the partial esterification of a bis(cyclic anhydride) compound ("dianhydride") with an organopolysiloxane bearing silanol or carbinol groups or their sulfur analogs, under conditions where only partial esterification occurs.

DETAILED DESCRIPTION

The carboxylic acid functional organopolysiloxanes of the invention are prepared by the reaction of a dianhydride with an organopolysiloxane having two hydroxyl or sulfhydryl groups. Preferably, the dianhydride is also an organopolysiloxane. The reaction is generally and preferably uncatalyzed, and may occur at any temperature which facilitates the ring opening reaction of the anhydride groups of the dianhydride to form ester-linked alkylene carboxylic acid groups of the formulae Ia, Ib:

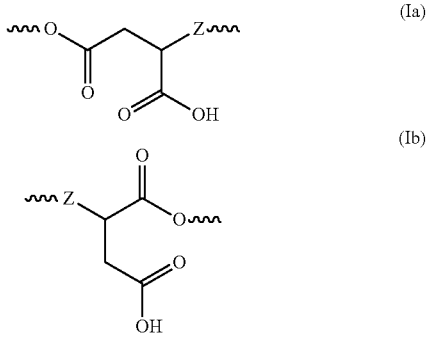

where Z is the residue of the dianhydride. By "residue of the dianhydride" is meant the remainder of the dianhydride compound, less its two anhydride groups.

The dianhydride is a compound bearing two cyclic anhydride groups. The cyclic anhydride groups are linked to the dianhydride residue by sharing carbon atoms of a ring structure, or by being attached at an aliphatic carbon atom, or through a hydrocarbon group, which may be aliphatic or aromatic. A five-membered cyclic anhydride group has the formula:

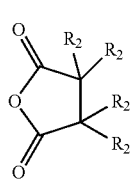

(II)

For succinic anhydride, for example, each $R^2$ is H, while for methyl succinic anhydride, one $R^2$ is methyl. For itaconic anhydride, two $R^2$s together form a methylene group. In the dianhydrides of the invention, either one $R^2$ constitutes a single bond to the dianhydride residue, or two vicinal $R^2$s constitute bonds to the dianhydride residue, which form a ring structure and may constitute an alicyclic or aromatic ring. In this case, the "Z" residue will also be bonded to an adjacent carbon atom of the structures Ia and Ib.

The dianhydride residue may be any suitable residue which is attached to the two anhydride groups, preferably a low molecular weight hydrocarbon or oligomeric siloxane, or an organic polymer or organopolysiloxane. Dianhydrides where the cyclic anhydride groups are attached to an alicyclic or aromatic ring such as the phthalic anhydride group are preferred as non-organopolysiloxane residue dianhydrides. Numerous dianhydrides are known, and many have been used to manufacture high temperature-resistant polyimides. Examples are pyromellitic dianhydride, 4,4'-oxydiphthalic anhydride, bisphenol A diphthalic anhydride, 1,2,4,5 cyclohexane tetracarboxylic acid dianhydride, 3,3',4,4'-biphenyltetracarboxylic acid dianhydride, 3,3',4,4'-benzophenone tetracarboxylic acid dianhydride, 1,2,3,4-cyclopentanetetracarboxylic acid dianhydride, 1,4,5,8-naphthalene tetracarboxylic acid dianhydride, 1,2,3,4-cyclobutanetetracarboxylic acid dianhydride, ethylenediaminetetracarboxylic acid dianhydride, bicyclo[2.2.2]-oct-7-ene-2,3,5,6-tetracarboxylic acid dianhydride, and the like.

Preferred, however, are dianhydrides having two cyclic anhydride groups present as terminal groups of an organopolysiloxane. Such organopolysiloxanes may have, for example, terminal alkylphthalic anhydride groups or terminal succinic anhydride or alkylsuccinic anhydride groups, for example. Any organopolysiloxane bearing two cyclic anhydride groups is suitable. These anhydride groups are preferably terminal groups. Preferred organo groups R of the organopolysiloxane residue of the organopolysiloxane dianhydride are hydrocarbon groups or Si—C bonded alkyl-terminated polyoxyalkylene groups which are conventionally used in organopolysiloxane chemistry. The R groups are preferably alkyl, more preferably $C_{1-18}$ alkyl, more preferably $C_{1-4}$ alkyl, and most preferably methyl, $C_{4-18}$ cycloalkyl or are $C_{7-20}$ aralkyl, alkaryl, or $C_{6-18}$ aryl groups, preferably phenyl groups. It is also possible, but not preferred, that the organopolysiloxane dianhydrides contain silicon-bonded alkoxy groups, preferably $C_{1-4}$ alkoxy groups, and more preferably methoxy or ethoxy groups. The anhydride groups are preferably carbon bonded to silicon atoms, more preferably to terminal silicon atoms of the organopolysiloxane dianhydride. The bonding may be directly to a carbon atom of the anhydride group, or may be to the anhydride group through the intermediary of a hydrocarbon(oxy) group, preferably an aryl group, an aralkyl group, or an alkyl (alkylene) group. Preferred organopolysiloxane dianhydrides have the formulae

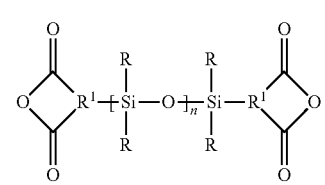

(III)

where R is defined previously, n is an integer of from 1 to 1000, preferably 1 to 500, more preferably 10 to 100, and $R^1$ is a trivalent aromatic radical, preferably a $C_{6-18}$ aryl group; and

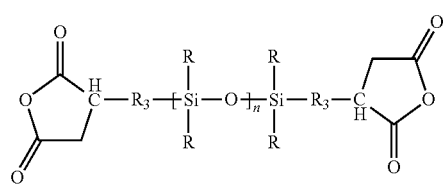

(IV)

where R and n are as defined above, and $R^3$ is a $C_{1-18}$ hydrocarbonoxy linking group, preferably a $C_{1-18}$ hydrocarbon linking group, preferably a $C_{1-8}$ alkylene group, more preferably a $C_{1-3}$ alkylene group, and most preferably a methylene or propylene group, and when $R^3$ contains two or more carbon atoms, adjacent carbon atoms may be interrupted by non-adjacent oxygen atoms. Two such organopolysiloxane dianhydrides are available from Wacker Chemie as organopolysiloxane IM 86, and from Gelest as DMS-Z21.

The anhydride-reactive organopolysiloxanes contain silicon bonded hydroxyl groups, e.g. terminal silanol groups, or preferably, terminal carbinol groups. Thus, the anhydride-reactive organopolysiloxane is preferably one of the formula:

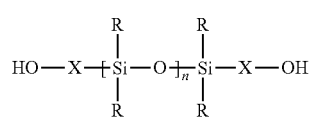

(V)

where R and n are as previously defined, and X is a chemical bond or a $C_{1-18}$ alkylene group, more preferably a $C_{1-6}$ alkylene group, and most preferably a methylene or propylene group, particularly a propylene group. The corresponding sulfhydryl and mercaptoalkyl analogs are also useful, and produce the corresponding thioesters upon reaction with the dianhydride.

Also preferred are compounds where X is the residue of an oxyalkylene group, preferably a group of the formula:

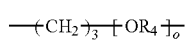     (VI)

where R is alkylene, preferably $C_{2-4}$ alkylene, and most preferably ethylene or propylene, and o is an integer from 1 to 100, more preferably 2 to 50, and yet more preferably 2 to 25. Such groups, together with the terminal carbinol OH group, may be prepared, for example, by oxyalkyating a propanol-terminated organopolysiloxane, preferably with ethylene oxide, propylene oxide, or mixtures thereof, in any fashion, e.g. randomly or in block form, or by hydrosilylating an allyl ether-terminated polyoxyalkylene glycol with an organopolysiloxane bearing Si—H functionality.

The silanol-terminated organopolysiloxanes are well known items of commerce, and are available with a wide number of repeating diorganosiloxy units, and hence viscosities. The preferred carbinol-functional organopolysiloxanes are also commercially available, and may be prepared, for example, by the hydrosilylation of an alkenol such as allyl alcohol or hexadecene-1-ol with an α-ω-bis(hydrogendiorganosilyl)-terminated organopolysiloxane.

The reaction between the dianhydride and the dianhydride-reactive organopolysiloxane may take place neat, or in organic solvent, preferably neat. No catalyst is necessary, although it would not depart from the spirit of the invention to add a catalyst, so long as the catalyst is not active under the reaction conditions so as to cause significant esterification of the pendent carboxylic acid groups formed. The reaction preferably takes place at elevated temperature, for example from 40° C. to 99° C., more preferably from 60° C. to 95° C., and most preferably from 70° C. to 95° C. The reaction preferably is not conducted at temperatures of 100° C. or more at atmospheric pressure, to avoid removing water and hence promoting the esterification of pendent carboxylic acid groups formed by ring-opening (half) esterification of the cyclic anhydride groups. However, higher temperatures may be used, if necessary, under an increased pressure, below the boiling point of water at that pressure. Moreover, esterification of a portion of the pendent hydroxyl groups, e.g. less than 20 mol percent based on the theoretical number of pendent carboxylic acid groups which could be present, while undesirable, is within the scope of the invention. Branched products would result from this reaction. The reaction preferably takes place with the exclusion of water. Organic solvents such as toluene may be used, but their use is neither necessary nor preferred. The reactions are preferably neat reactions.

More than one type of dianhydride may be used, and/or more than one type of silanol- or carbinol-functional organopolysiloxane or sulfur-containing analog thereof may be used. Furthermore, in addition to these ingredients, it is also possible to include other anhydride-reactive compounds as co-reactants.

As a result of the ring-opening esterification, the products of the reaction between the dianhydride and the anhydride-reactive organopolysiloxane generally have repeating units of the structure:

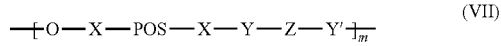     (VII)

where X is defined previously, m is from 1 to 1000, more preferably 1 to 100, and most preferably 2-10, POS is the organopolysiloxane residue of the silanol- or carbinol-functional organopolysiloxane or its sulfur analog, Z is the residue of the dianhydride, preferably an organopolysiloxane residue, and Y and Y', respectively, are half-diesters of the formulae:

     (VIIIa)

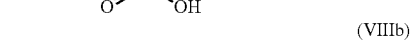     (VIIIb)

The carbon atoms located between the carbonyl moieties of these groups may optionally be substituted, e.g. by alkyl or aryl groups, preferably methyl groups. Preferably these linking groups are unsubstituted or substituted by a single methyl group α or β to the carbonyl carbon of the ester group, as in methylsuccinic anhydride groups. The groups may be oriented as shown, or reversed.

The products of the reaction will be anhydride-terminated when an excess of dianhydride is used, and will be silanol or carbinol-terminated when an excess of silanol- or carbinol-functional organopolysiloxane is used. When sulfur analogs of the silanol or carbinol-terminated organopolysiloxanes are used, the polymers may be terminated by silicon-bonded—SH groups or mercaptoalkyl groups. The molecular weight and end group functionality can be adjusted by the stoichiometric ratio of dianhydride groups to carbinol and/or silanol groups. Higher molecular weights are generated the closer the stoichiometric ratio is to a 1:1 ratio. In the case of anhydride-terminated polymers, the terminal anhydride groups may be converted to carboxylic acid groups by ring-opening hydrolysis. Two such carboxylic acid groups will be formed by the hydrolysis, which can be accerated by catalysts, if necessary, such as acid catalysts or fluoride.

If non-functional terminal groups are desired, or if functional terminal groups with other than carboxylic acid, anhydride, silanol, carbinol, sulfhydryl or mercaptoalkyl groups are desired, then "chain stoppers" which are mono-functional anhydrides or mono-functional anhydride-reactive compounds may be added, depending upon whether the dianhydride compound or the silanol- or carbinol-functional compound or sulfur analog thereof is present in stoichiometric excess. The addition of mono-functional anhydrides or anhydride-reactive compounds during polymerization can be used to limit the product molecular weight.

For example, if the polymer is prepared from a stoichiometric excess of dianhydride, anhydride terminal groups may be converted to amide or ester groups by reaction with a monosilanol, alcohol, phenol, primary or secondary monoamine or other compound bearing a single reactive hydroxyl group, amino group, or other anhydride-reactive group such as a monoepoxy-functional compound, and if the silanol- or carbinol-functional siloxane or sulfur analog thereof is present in excess, a chain terminator reactive therewith, for example, but not by limitation, a monoisocyanate such as phenyl isocyanate or butyl isocyanate may be used. Further, if the silanol- or carbinol-functional organopolysiloxane or sulfur analog thereof is used in excess, a monoanhydride such as maleic anhydride, or a monoanhydride-functional organopolysiloxane or other compound, such as a monoanhydride-functional polymer, may be employed. The result is chain termination with one of the half-ester linkages described previously.

Functional chain stoppers such as glycidoxydimethylmethoxysilane, methacryloyloxydimethylmethoxysilane and the like may also be used. For example, self-emulsifying epoxy-functional silicones can be prepared in this manner. Such products offer the ability of self-crosslinking upon addition of a catalyst which accelerates the reaction of epoxy and carboxyl groups, for example bases, preferably organic bases such as pyridine, imidazoles, and organic amines. Cure preferably takes place at temperatures above 140° C.

In addition to reactive functional groups which may result by using a stoichiometric excess of dianhydride or anhydride-functional silicone, or by chain terminating with a chain terminating agent containing a reactive functional group other than anhydride, silanol, or carbinol, it is also possible to employ dianhydrides whose dianhydride residue itself contains functional groups, to employ silanol- or carbinol-functional organopolysiloxanes whose organopolysiloxane residue bears such functional groups, or both. Among the functional groups are blocked isocyanate groups, (meth)acrylate groups, other ethylenically unsaturated groups, etc. Thus, the process can be used to prepare a large number of reactive, self-emulsifying organopolysiloxanes. Such products have particular use in curable coatings.

The products of the invention, bearing regularly spaced pendent carboxylic acid groups, may be used as such, or may be reacted with a base to form the corresponding salts of the pendent carboxylic acid groups. Suitable counterions for the salts are, for example, alkali metal ions, in particular sodium and potassium ions, ammonium ions, and organoammonium ions. Use may be made, for example, of sodium hydroxide or potassium hydroxide, or potassium or sodium carbonates or bicarbonates, organophosphines, ammonia, organoamines such as methylamine, dimethylamine, trimethylamine and their higher alkyl analogs, preferably triethylamine, and the like. Organoamines are preferred in some applications. Not all the carboxylic acid groups need be converted to carboxylate salts.

Aqueous emulsions may be prepared from the products of the invention by numerous methods widely known to those skilled in the art of silicone emulsions. For example, the pendent carboxylic acid products may be first neutralized by formation of the corresponding carboxylate salts by simple stirring with a neutralizing agent such as triethylamine or aqueous alkali metal hydroxide, and then emulsified in water, or the non-neutralized or partially neutralized products may be stirred with water and the neutralizing agent subsequently added. Products with large numbers of carboxylic acid groups per molecule, prepared from low molecular weight dianhydrides and low molecular weight silanol- or carbinol-functional organopolysiloxanes (or sulfur analogs thereof) may not require neutralization to form stable emulsions, or may do so when only minimally neutralized, e.g. while still in the acid range. For most products, the aqueous pH of the emulsion will be ≥6.5, preferably ≥7.0, more preferably ≥7.5, and most preferably in the range of 7.5-9.0. The maximum pH is not especially limited, but is preferably less than 13.0, more preferably less than 12.0, yet more preferably less than 11.0, and most preferably within the range of 9.5-10.5.

It is noteworthy that the emulsions can be prepared by simple stirring. High shear devices such as colloid mills, homogenizers, and high shear rotor/stator mixers are not necessary, although these may be used when very small particle sizes of the dispersed phase is desired. Methods of inverse emulsion preparation may also be used.

The products of the invention have numerous uses, for example as conditioning and glossing agents for rubber products, hard surface gloss enhancers and sealers, fiber and textile treatment, and the like. The products may also be used as hydrophobing agents for cementitious and non-cementitious building chemicals such as renders, mortars, adhesives, etc., and for wood, paper, cardboard, and the like. One particularly preferred use is in anti-fogging coatings.

By "stable aqueous emulsion" is meant an emulsion which does not separate into an oily phase after storage at room temperature for one week. A highly stable emulsion is one which does not readily cream, and in the event of creaming, is re-emulsifyable by simple stirring or shaking Preferably, the emulsions exhibit no oil phase separation and no creaming after storage for one month at 25° C. The foregoing stabilities are those of aqueous emulsions containing no surfactant, or less than 1 weight percent surfactant, based on the total weight of the aqueous emulsion. Emulsions preferably contain <5 weight percent of emulsifiers based on the total weight of the emulsion, more preferably less than 3%, yet more preferably less than 2%, still more preferably less than 1%. Emulsions are most preferably free of surfactants.

The products of the invention are noteworthy for having a regular alternating structure with regular distribution of pendent carboxylic acid groups. By "regularly spaced" is meant an essentially or completely non-random spacing which is predominately determined by the chain length of the dianhydride and the silanol- or carbinol-functional organopolysiloxane. The preferred products are thus preferably block-type polymers with blocks derived from the dianhydride residue(s) and the anhydride-reactive component residue(s), with pendent carboxylic groups positioned between adjacent blocks. The regular spacing results in improved mechanical stability of emulsions prepared from the products, and improved freeze/thaw resistance. Furthermore noteworthy is that films prepared from the inventive products exhibit reduced water sensitivity, and that the inventive products have improved compatibility with other film formers. This is especially the case in view of the preferable absence of surfactants.

In the Examples below, all amounts are by weight, temperature is room temperature, e.g. between 20° C. and 25° C. or at a temperature which results from the mixing of components with no additional heating or cooling unless otherwise noted, and all pressures are the pressure of the surrounding atmosphere, approximately 1013 hPa. All products were clear liquids, ranging in color from colorless to slightly amber. Brookfield viscosities are measured with a #4 spindle at 25° C. and 40 $s^{-1}$ revolution rate.

Example 1

To a glass reaction flask equipped with blade stirrer and thermometer is added 81.7 g of a silanol-terminated polydimethylsiloxane having a molecular weight of approximately 1130 g/mol and 318.3 g of a polydimethylsiloxane dianhydride bearing terminal propylsuccinic acid groups, having a molecular weight of about 4419 g/mol. The flask is heated to 90° C. and stirred for four hours. An organopolysiloxane product containing pendent carboxylic acid groups is obtained, having a viscosity of 265 cps at 40 s$^{-1}$ (#4 spindle), a number average molecular weight of 3964 Da, and a weight average molecular weight of 7898 Da.

Example 2

To 10.8 g of the product of Example 1 is added 0.6 g of triethylamine, with vigorous stirring, and then 25 parts of dionized water is added. A white, slightly foamy aqueous emulsion having a pH of 9.1 and a solids content of about 30 weight percent is formed.

Example 3

The process of Example 1 is followed, but employing 257.0 g of a 3500 g/mol silanol-terminated polydimethylsiloxane instead of the 81.7 g of the 1130 g/mol silanol-terminated polydimethylsiloxane. The reaction mixture is stirred for three hours at 90° C. rather than for four hours. A organopolysiloxane with pendent carboxylic acid groups is obtained.

Example 4

The product of Example 3, 30.0 g, is stirred vigorously with a vane-type stirrer with 1.4 g of triethylamine, and 69.0 g of water is added. A white emulsion containing approximately 30 weight percent solids and a pH of 8.9 is obtained.

Example 5

The process of example 1 is followed, but the reactants are 441.9 g of the polydimethylsiloxane dianhydride and 224.4 g of a polydimethylsiloxane containing approximately 17 dimethylsiloxygroups, terminated at both ends with an Si—C-bonded 3-hydroxypropyl group, then oxyethylated with 10 moles of ethylene oxide. The carbinol terminal functionality is thus 2-hydroxyethyl. The 90° C. reaction is terminated after four hours. A organopolysiloxane bearing pendent carboxylic acid groups is obtained.

Example 6

Water in an amount of 250.7 g is added to 108.1 g of the product of Example 5 and stirred vigorously with an impeller-type stirrer, and 1.6 g triethylamine is added. The pH is still on the acid side, and 1.8 g additional triethylamine is added, resulting in a viscous emulsion with a pH of 7.2. To this emulsion, a further 1.4 g triethylamine and an additional 95 g of water is added to form an approximately 30% solids aqueous emulsion with a pH of 8.5.

Example 7

In a manner similar to Example 1, 6.7 g ethylene glycol is reacted with 318.3 g of the polydimethylsiloxane dianhydride with molecular weight of 4419 g/mol, a polyol/dianhydride mol ratio of 1.23. A carbinol-functional organopolysiloxane bearing pendent carboxylic acid groups is obtained. The product has a Brookfield viscosity of 265 cps, $M_n$ 6499 Da, $M_w$ 13,340 Da.

Example 8

Example 7 is repeated, but employing 86.5 g of a linear bis(propanol)-terminated organopolysiloxane having 11 repeating dimethylsiloxy groups instead of ethylene glycol, an 300 g of the polydimethylsiloxane dianhydride at a polyol/dianhydride ratio of 1.02. A product containing carbinol functionality is obtained. Brookfield viscosity 2875 cps, $M_n$ 14,125 Da, $M_w$ 33,650 Da.

Example 9

Example 7 is repeated, but employing anhydride groups. The ratio of OH groups to 78 g of bis(propanol)-terminated polydimethylsiloxane having 11 repeating siloxy groups, 300 g of polydimethylsiloxane dianhydride used in Example 1, and 0.53 g glycerine. The pendent carboxylic acid group-containing slightly branded product had a Brookfield viscosity of 2765 cps, Mn 13,191, and $M_w$ 28,153.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A non-crosslinked, linear organopolysiloxane bearing a plurality of non-terminal chain-pendent carboxylic-acid groups and non-terminal in-chain ester groups, prepared by a process comprising:
   a) reacting one or more difunctional, anhydride-reactive components comprising linear organopolysiloxanes bearing two terminal silanol groups or two terminal carbinol groups, with
   b) a dianhydride component comprising two terminal cyclic dicarboxylic acid anhydride groups,
   reacting taking place under conditions such that at least 80 mol percent of chain-pendent carboxylic acid groups resulting from a ring-opening esterification of silanol groups or carbinol groups and cyclic anhydride groups remain non-esterified, and wherein non-esterified carboxylic acid groups are optionally present in the form of a carboxylate salt.

2. The non-crosslinked, linear organopolysiloxane of claim 1, wherein the non-crosslinked linear organopolysiloxane bearing a plurality of non-terminal chain-pendent carboxylic acid groups and non-terminal in-chain ester groups comprises at least one group of the formula (VII):

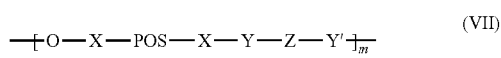

where X is a covalent bond or a difunctional alkylene group having from 1 to 18 carbon atoms, POS is a polyorganosiloxane residue of the silanol- or carbinol-terminated organopolysiloxane, Z is a residue of the dianhydride, and m is from 2 to 1000, and Y and Y', respectively, are half-diesters of the formulae:

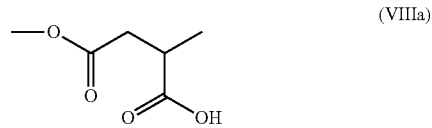

(VIIIb)

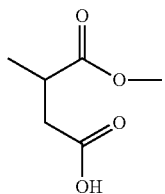

3. The non-crosslinked, linear organopolysiloxane of claim 1, wherein the non-crosslinked linear organopolysiloxane bearing a plurality of non-terminal chain-pendent carboxylic acid groups and non-terminal in-chain ester groups comprises at least one group of the formula (VII):

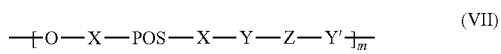 (VII)

where X is a covalent bond or a difunctional alkylene group having from 1 to 18 carbon atoms, POS is a polyorganosiloxane residue of the silanol- or carbinol-terminated organopolysiloxane, Z is a residue of the dianhydride, and m is from 2 to 10, and Y and Y', respectively, are half-diesters of the formulae:

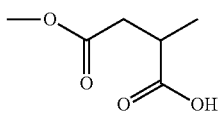 (VIIIa)

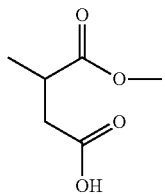 (VIIIb)

4. The non-crosslinked, linear organopolysiloxane of claim 1, wherein the non-crosslinked linear organopolysiloxanes bearing a plurality of non-terminal chain-pendent carboxylic acid groups and non-terminal in-chain ester groups comprises at least one group of the formula (VII):

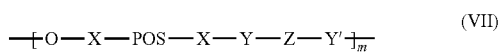 (VII)

where X is a covalent bond or a difunctional alkylene group having from 1 to 18 carbon atoms, POS is a polyorganosiloxane residue of the silanol- or carbinol-terminated organopolysiloxane, Z is a residue of the dianhydride, and m is from 10 to 100, and Y and Y', respectively, are half-diesters of the formulae:

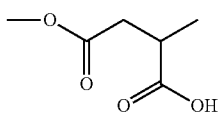 (VIIIa)

(VIIIb)

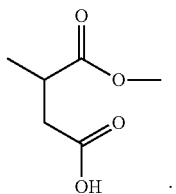

5. The non-crosslinked linear organopolysiloxane of claim 1, wherein the dianhydride component comprises a dianhydride with two terminal cyclic carboxylic anhydride groups linked by a hydrocarbon group or by an organic polymer.

6. The non-crosslinked linear organopolysiloxane of claim 1, wherein the dianhydride component comprises an organopolysiloxane bearing two terminal cyclic anhydride groups.

7. The non-crosslinked linear organopolysiloxane of claim 1, wherein the difunctional anhydride-reactive component comprises only organopolysiloxanes bearing two terminal silanol groups.

8. The non-crosslinked linear organopolysiloxane of claim 1, wherein the difunctional anhydride-reactive component a) is used in molar excess with respect to the cyclic dianhydride to form a silanol- or carbinol-terminated organopolysiloxane, and a mono-functional cyclic anhydride is used to form dicarboxylic acid half-ester terminal groups.

9. The non-crosslinked linear organopolysiloxane of claim 1, wherein the cyclic dianhydride is used in molar excess with respect to the difunctional anhydride-reactive component to form an anhydride-terminated organopolysiloxanes, and a monofunctional silanol or carbinol is used to form siloxyl or carbinoyl terminal groups.

10. The non-crosslinked linear organopolysiloxane of claim 1, wherein the cyclic dianhydride is used in molar excess with respect to the difunctional anhydride-reactive component to form an anhydride-terminated organopolysiloxanes, and terminal anhydride groups are reacted with a monosilanol, alcohol, or phenol to form an ester-terminated organopolysiloxane, or are reacted with a primary or secondary monoamine to form an amide-terminated organopolysiloxanes.

11. The non-crosslinked linear organopolysiloxane of claim 1, wherein at least a portion of non-esterified chain-pendent carboxylic acid groups are in the form of a carboxylate salt.

12. The non-crosslinked linear organopolysiloxane of claim 11, wherein the carboxylate salt contains counterions of one or more of alkali metal ions, the ammonium ion, or organoammonium ions.

13. The non-crosslinked linear organopolysiloxane of claim 1, wherein the organopolysiloxane is further reacted with a functional chain stopper comprising a functionality other than carbinol, silanol, anhydride, or dicarboxylic acid half ester.

14. The non-crosslinked linear organopolysiloxane of claim 13, wherein the functional chain stopper comprises at least one functional group selected from the group consisting of ethylenically unsaturated groups, blocked isocyanate groups, (meth)acrylate groups, and epoxy groups.

15. The non-crosslinked linear organopolysiloxane of claim 1, wherein carboxylate salts are not present, and the organopolysiloxanes contains a sufficient number of free carboxylic acid groups such that the organopolysiloxanes is self-emulsifying in an aqueous medium to form an aqueous emulsion, or forms an aqueous emulsion with less than 5 weight percent of organic emulsifiers based on the weight of the aqueous emulsion.

16. The non-crosslinked linear organopolysiloxane of claim 1, which forms an aqueous emulsion without any organic emulsifier, or with less than 5 weight percent of organic emulsifiers, based on the weight of the aqueous emulsion.

17. The non-crosslinked linear organopolysiloxane of claim 1, which contains regularly spaced pendent carboxylic acid groups and/or salts thereof.

18. The non-crosslinked linear organopolysiloxane of claim 17, wherein a single difunctional anhydride-reactive organopolysiloxanes is employed as the difunctional anhydride-reactive component.

19. The non-crosslinked linear organopolysiloxane of claim 18, wherein a single dianhydride component is employed.

20. A branched organopolysiloxane comprising a plurality of non-terminal pendent carboxylic acid groups and a plurality of non-terminal in-chain ester groups, prepared by forming a non-crosslinked, linear organopolysiloxane of claim 1, and heating and removing water to form ester-linked branch sites, esterification involving no more than 20 mol percent of the pendent carboxylic acid groups present in the non-crosslinked, linear organopolysiloxane.

* * * * *